United States Patent [19]

Siciliano et al.

[11] 3,998,865

[45] Dec. 21, 1976

[54] PROCESS FOR THE STABILIZATION OF HEXAMETHYL-CYCLOTRISILOXANE AND THE STABILIZED COMPOSITIONS RESULTING THEREFROM

[75] Inventors: George R. Siciliano, Ballston Lake; Verne G. Simpson; James J. Finigan, both of Mechanicville, all of N.Y.

[73] Assignee: General Electric Company, Waterford, N.Y.

[22] Filed: Mar. 12, 1975

[21] Appl. No.: 557,604

[52] U.S. Cl. .......................................... 260/448.2 S
[51] Int. Cl.$^2$ ........................................... C07F 7/08
[58] Field of Search ............................. 260/448.2 S

[56] References Cited

UNITED STATES PATENTS

| | | | |
|---|---|---|---|
| 2,465,296 | 3/1949 | Swiss | 260/448.2 S X |
| 2,739,952 | 3/1956 | Linville | 260/448.2 S X |
| 2,928,857 | 3/1960 | Holt et al. | 260/448.2 S X |
| 2,962,446 | 11/1960 | Cook | 260/448.2 S X |

*Primary Examiner*—Paul F. Shaver
*Attorney, Agent, or Firm*—Donald J. Voss; Edward A. Hedman; Rocco S. Barrese

[57] ABSTRACT

A process for stabilizing hexamethylcyclotrisiloxane is provided, said process involving the intimate admixture of hexamethylcyclotrisiloxane and an alkaline earth oxide, such as magnesium oxide (MgO). The resultant stabilized compositions are also encompassed herein.

22 Claims, No Drawings

PROCESS FOR THE STABILIZATION OF HEXAMETHYL-CYCLOTRISILOXANE AND THE STABILIZED COMPOSITIONS RESULTING THEREFROM

BACKGROUND OF THE INVENTION

This invention relates to organosilicone compositions and processes and more particularly to a process for the stabilization of hexamethylcyclotrisiloxane and the stabilized compositions resulting therefrom.

Hexamethylcyclotrisiloxane $(CH_3)_2SiO)_3$ is a useful intermediate in the preparation of higher molecular weight poly(alkylsiloxane) fluids and gums which in turn have a wide variety of well-known uses, such as, for example, caulking and molding compositions.

Hexamethylcyclotrisiloxane, a solid at room temperature (m.p. 64° C), is a considerably unstable material and prolonged standing and/or storage of the material, either in solid or molten form, results in spontaneous polymerization to undesirable high viscosity materials. Because of its use as an intermediate for subsequent reaction, hexamethylcyclotrisiloxane is generally stored, mostly for convenience purposes, in the molten state, i.e., maintained at a temperature above about 64° C, its melting point, and below about 134° C, its boiling point. The spontaneous polymerization to high viscosity materials occurs at even a faster rate when the material is stored in the molten state.

Although it is not known for certain, it is believed that the spontaneous polymerization which occurs in unstabilized hexamethylcyclotrisiloxane is caused by acidic impurities and/or ionic chloride impurities which are generally present as a result of its method of preparation. Attempts to preven the spontaneous polymerization resulting from these impurities using basic materials such as sodium bicarbonate, have not adequately stabilized the material. That is, it has been found that in the presence of sodium bicarbonate the spontaneous polymerization of the hexamethylcyclotrisiloxane proceeds at a reduced rate but is insufficient to provide adequate storage stability over an extended period.

Because of its instability, hexamethylcyclotrisiloxane is presently not stored for any length of time but generally, out of necessity, must be reacted to higher viscosity material almost immediately after its preparation.

Thus, as a result of the large quantities of hexamethylcyclotrisiloxane manufactured each year, a need has developed for a method to stabilize it, primarily to allow the material to be adequately stored without the loss of large quantities.

SUMMARY OF THE INVENTION

Accordingly, it is one object of this invention to provide a process to stabilize hexamethylcyclotrisiloxane.

Another object of this invention is to provide stabilized compositions of hexamethylcyclotrisiloxane.

These and other objects are achieved herein by providing a process comprising intimately admixing an alkaline earth oxide with hexamethylcyclotrisiloxane and by providing the stabilized compositions, i.e., alkaline earth oxide and hexamethylcyclotrisiloxane, resulting therefrom.

DETAILED DESCRIPTION OF THE INVENTION

In accordance with the present invention, an alkaline earth oxide is intimately admixed with the hexamethylcyclotrisiloxane. The method of mixing the two materials may be performed in a variety of ways. For example, one way simply involves thoroughly blending, such as, for example, in a Waring type blender, the solid alkaline oxide powder with the solid hexamethylcyclotrisiloxane. Another way involves preparing a solution, slurry or dispersion of the alkaline oxide powder in a suitable carrier and subsequently intimately admixing the resultant solution, slurry or dispersion with the solid hexamethylcyclotrisiloxane in, for example, a Waring type blender or any other type of agitating means which will ultimately provide intimate admixture.

A preferred method to prepare the present stabilized compositions, however, involves admixing the solid alkaline earth oxide powder with molten hexamethylcyclotrisiloxane (i.e., the hexamethylcyclotrisiloxane is at a temperature between above about 64° C and below about 134° C). This method is desirable for several reasons, including the facts that a more intimate admixture of the materials is achieved in this manner and also that the hexamethylcyclotrisiloxane is conveniently stored in the molten state.

The method most preferred herein for providing stabilized compositions of hexamethylcyclotrisiloxane involves the intimate admixture of a solution, slurry or dispersion of the alkaline earth powder with molten hexamethylcyclotrisiloxane. This method provides for the most intimate contact of the two materials and concomitantly provides for the best stabilization of the hexamethylcyclotrisiloxane.

Included among the suitable alkaline earth oxides which are encompassed herein are, for example, magnesium oxide (MgO), calcium oxide (CaO), barium oxide (BaO) and the like. Magnesium oxide is most preferred.

As mentioned heretofore, the alkaline earth oxides may be used in powder or other solid form directly, or they may be utilized in a solution, slurry or dispersion by admixture with a suitable carrier. Thus, a wide variety of liquid carrier materials are suitable for this purpose. Included among these are inert liquids such as, for example, organic hydrocarbons like xylene, toluene, benzene, hexane, pentane, and the like. Other inert liquids useful as carriers for the alkaline earth oxides herein include water and low viscosity silicone oils, such as low viscosity poly(alkylsiloxanes) like low viscosity poly(dimethylsiloxanes) and low viscosity silanol-terminated poly(dimethylsiloxanes). By low viscosity, it is generally meant a fluid of from about 5 to about 100 centipoises at 25° C with a range of from about 20–50 being preferred. The low viscosity silanol terminated poly(dimethylsiloxanes) are preferred.

Since several of the preferred embodiments of this invention involve the utilization of molten hexamethylcyclotrisiloxane, it is preferred in these cases to use an inert carrier liquid which has a boiling point above the range of from about 64° C to about 134° C, or at least above the particular temperature at which the hexamethylcyclotrisiloxane is being maintained in molten form. A preferred temperature at which to maintain the hexamethylcyclotrisiloxane in molten form is from about 70°–100° C. For these purposes, the aforedescribed low viscosity poly(alkylsiloxane) oils are also preferred, particularly the low viscosity silanol terminated poly(dimethylsiloxanes).

In preparing a solution, dispersion or slurry of the alkaline oxide in the above-described inert liquid carriers, it is generally preferred for purposes of this invention to employ a ratio of from about 1 to 2 to 1 to 8 parts by weight of alkaline earth oxide to liquid carrier, respectively. A preferred ratio is about 1 part by weight alkaline oxide to 3 parts by weight of liquid carrier.

The effective amount of alkaline earth oxide necessary to provide adequate stabilization varies somewhat. In general, however, this amount is from about 10 parts per million (ppm) to about 2% by weight of hexamethylcyclotrisiloxane. A range of from about 50 to about 100 parts alkaline oxide per million parts of hexamethylcyclotrisiloxane is preferred, with about 50 parts alkaline oxide per million parts hexamethylcyclotrisiloxane being most preferred.

In order that those skilled in the art may better understand how the present invention may be practiced, the following examples are given by way of illustration and not by way of limitation.

EXAMPLE 1

300 grams of magnesium oxide (MgO) powder are mixed in a Waring blender with 600 grams of a silanol-stopped poly(dimethylsiloxane) having a viscosity of about 25–30 centipoises at 25° C. Mixing continues for several minutes until a reasonably flowable slurry is obtained. The resultant magnesium oxide slurry is then intimately mixed with 300 grams of molten (82° C) hexamethylcyclotrisiloxane (sufficient to provide 100 parts of magnesium oxide per million parts of hexamethylcyclotrisiloxane). The molten hexamethylcyclotrisiloxane has 8% polymerized material present initially. The resultant mixture is aged at 180° F for 10 days. After this period, analysis shows a total of 12% polymerized material present, i.e., only a 4% increase over the amount of polymer initially present.

EXAMPLE 2

Approximately 0.03 grams of magnesium oxide (MgO) powder is intimately admixed with 300 grams of molten (82° C) hexamethylcyclotrisiloxane (sufficient to provide 100 parts MgO per million parts of trimer). The hexamethylcyclotrisiloxane trimer used already has about 8% polymerized material present initially. The resultant mixture is aged at 180° F for 10 days. Analysis shows that after this period a total of about 12% polymerized material is present, i.e., an increase of only about 4%.

Substituting hexamethylcyclotrisiloxane containing substantially no polymerized material for the hexamethylcyclotrisiloxane containing an initial amount of 8% polymerized material in Examples 1 and 2 gives similar results to those obtained in Examples 1 and 2.

EXAMPLE 3

1 part by weight magnesium oxide powder is intimately admixed with 3 parts by weight of a silanol-stopped poly(dimethylsiloxane) having a viscosity of about 25–30 centipoises at 25° C. The resultant magnesium oxide slurry is then intimately admixed with molten hexamethylcyclotrisiloxane trimer in a ratio of about 90 grams of slurry to about 1000 lbs. of trimer to provide 50 ppm of magnesium oxide. The resultant hexamethylcyclotrisiloxane composition is stable against spontaneous polymerization.

The table below further illustrates the unexpected and desirable results obtained by the present invention.

Table

| Composition | % high viscosity polymer initially present | % high viscosity polymer after 10 days' storage at 180° F | Difference in % high viscosity polymer after 10 days' storage |
|---|---|---|---|
| Example 1 | 8 | 12 | 4 |
| Example 2 | 8 | 12 | 4 |
| Molten hexamethylcyclotrisiloxane (no additives) | 8 | 53 | 45 |
| Molten hexamethylcyclotrisiloxane and sodium bicarbonate crystals (400 ppm) | 8 | 26 | 18 |
| Molten hexamethylcyclotrisiloxane and 200 ppm of the silanol stopped poly(dimethylsiloxane) used in Example 1 | 8 | 52 | 44 |

Thus, the above data clearly show that, surprisingly, the presence of an alkaline oxide, such as magnesium oxide, not only prevents spontaneous polymerization and loss of the hexamethylcyclotrisiloxane trimer but arrests any polymerization which may already have begun to occur in the unstabilized trimer.

It is understood, of course, that the use of molten hexamethylcyclotrisiloxane initially containing 8% polymerized material in some of the above examples and table is for convenience purposes and illustrative purposes only and that obviously hexamethylcyclotrisiloxane material containing substantially no polymerized material is within the intended scope of this invention.

Moreover, the substitution of calcium oxide or barium oxide for the magnesium oxide of Examples 1 and 2 provides similar results.

Obviously, other modifications and variations of the present invention are possible in light of the above teachings. It is therefore to be further understood that changes may be made in the particular embodiments of this invention which are within the full intended scope of the invention as defined by the appended claims.

What is claimed and desired to be secured by Letters Patent is:

1. A process for stabilizing hexamethylcyclotrisiloxane, said process comprising intimately admixing an effective stabilizing amount of an alkaline earth oxide selected from the group consisting of magnesium oxide, calcium oxide and barium oxide with said hexamethylcyclotrisiloxane.

2. The process defined in claim 1 wherein said hexamethyltrisiloxane is molten.

3. The process defined in claim 1 wherein said alkaline earth oxide is directly admixed with said hexamethylcyclotrisiloxane in the absence of a liquid carrier.

4. The process defined in claim 1 wherein said alkaline earth oxide is intimately mixed with an inert liquid carrier and the resultant mixture is intimately admixed with said hexamethylcyclotrisiloxane.

5. The process defined in claim 4 wherein said inert carrier is a polar liquid having a boiling point above 134° C and said hexamethylcyclotrisiloxane is molten.

6. The process defined in claim 5 wherein said alkaline earth oxide is magnesium oxide, and said liquid carrier is a low viscosity poly(dialkylsiloxane).

7. The process defined in claim 6 wherein said low viscosity poly(dialkylsiloxane) is a silanol-stopped poly(dimethylsiloxane).

8. The process defined in claim 7 wherein said magnesium oxide is present in an amount of from about 50 to about 100 parts per million parts of said molten hexamethylcyclotrisiloxane.

9. A stabilized hexamethylcyclotrisiloxane composition comprising an effective stabilizing amount of an alkaline earth oxide selected from the group consisting of magnesium oxide, calcium oxide and barium oxide in intimate admixture with hexamethylcyclotrisiloxane.

10. The stabilized composition of claim 9 wherein said hexamethylcyclotrisiloxane is molten.

11. The stabilized composition of claim 9 which comprises the intimate admixture of a mixture of said alkaline earth oxide in an inert liquid carrier and said hexamethylcyclotrisiloxane.

12. The stabilized composition of claim 9 wherein said alkaline earth oxide is magnesium oxide.

13. The stabilized composition of claim 10 wherein said alkaline earth oxide is magnesium oxide.

14. The stabilized composition of claim 11 wherein said alkaline earth oxide is magnesium oxide.

15. The stabilized composition of claim 11 wherein said inert liquid carrier is a liquid having a boiling point above about 134° C.

16. The stabilized composition of claim 14 wherein said hexamethylcyclotrisiloxane is molten.

17. The stabilized composition of claim 15 wherein said inert liquid is a low viscosity poly(dimethylsiloxane).

18. The stabilized composition of claim 16 wherein said liquid carrier is a low viscosity poly(dialkylsiloxane).

19. The stabilized composition of claim 18 wherein said low viscosity poly(dialkylsiloxane) is a silanol-stopped poly(dimethylsiloxane).

20. The stabilized composition of claim 18 wherein said magnesium oxide is present in an amount of from about 50 to 100 parts per million parts of said molten hexamethylcyclotrisiloxane).

21. A process for stabilizing hexamethylcyclotrisiloxane, said process comprising intimately admixing an alkaline earth oxide selected from the group consisting of magnesium oxide, calcium oxide and barium oxide with said hexamethylcyclotrisiloxane, said alkaline earth oxide being used in an amount ranging from about 10 parts per million to about 2% by weight of said hexamethylcyclotrisiloxane.

22. The process defined in claim 21 wherein the amount of said alkaline earth oxide is from about 50 to about 100 parts per million of said hexamethylcyclotrisiloxane.

* * * * *

UNITED STATES PATENT OFFICE
CERTIFICATE OF CORRECTION

Patent No. 3,998,865    Dated December 21, 1976

Inventor(s) G. R. Siciliano et al

It is certified that error appears in the above-identified patent and that said Letters Patent are hereby corrected as shown below:

Claim 2, "hexamethyltrisiloxane" should read
--hexamethylcyclotrisiloxane--

Signed and Sealed this

Nineteenth Day of April 1977

[SEAL]

Attest:

RUTH C. MASON
Attesting Officer

C. MARSHALL DANN
Commissioner of Patents and Trademarks